United States Patent [19]

McDonough et al.

[11] Patent Number: 5,607,670
[45] Date of Patent: Mar. 4, 1997

[54] SEX ATTRACTANT FOR THE CRANBERRY FRUITWORM

[75] Inventors: Leslie M. McDonough; Harry G. Davis; Constance L. Smithhisler, all of Yakima, Wash.

[73] Assignee: The United States of America as represented by the Secretary of Agriculture, Washington, D.C.

[21] Appl. No.: 432,923

[22] Filed: May 1, 1995

[51] Int. Cl.$^6$ ............................ A01N 25/00; C07C 67/02
[52] U.S. Cl. ................................. 424/84; 560/261
[58] Field of Search ............................. 560/261; 424/84

[56] References Cited

PUBLICATIONS

J. of Chem. Ecology, McDonough et al., "Sex Pheromone of Cranberry Fruitworm, Acrobasis Vaccinii", 1004, pp. 3269–3279, abstract, 1994.
Handbook of Insect Pheromones and Sex Attractants, Mayer et al., 1991, p. 35.
Bestmann et al., "Synthesis of Conjugated . . . Analogues", Liebigs Ann. Chem., pp. 2117–2138. 1981.

T. Ando, S. Yoshida, S. Tatsuki, and N. Takahashi, "Sex Attractants for Male Lepidoptera," *Agricultural and Biological Chemistry* vol. 41, No. 8, pp. 1485–1492 (1977).
M. S Mayer, and J. R. McLaughlin, *Handbook of Insect Pheromones and Sex Attractants.* CRC Press Inc., Boca Raton, Florida (1991), p. 35.
W. E. Tomlinson, "Control of the Cranberry Fruitworm, *Acrobasis vaccinnii,*" *Journal of Economic Entomology,* 53:1116–1119 (1960).

Primary Examiner—Gary Geist
Assistant Examiner—Rosalynd A. Williams
Attorney, Agent, or Firm—M. Howard Silverstein; John D. Fado; Margaret A. Connor

[57] ABSTRACT

A composition of two compounds, (E,Z)-8,10-pentadecadien-1-ol acetate and (E)-9-pentadecen-1-ol acetate, is a highly effective attractant for the male cranberry fruitworm. The novel composition provides a sensitive tool for detection of this pest. By attracting male cranberry fruitworm moths to field traps, the composition provides a means for detecting, surveying, monitoring, and controlling the cranberry fruitworm. The attractant composition can also be used as a direct control tool by dispensing it throughout the host crop canopy, thereby preventing male cranberry fruitworms from locating and mating with the females.

11 Claims, 2 Drawing Sheets

5,607,670

SEX ATTRACTANT FOR THE CRANBERRY FRUITWORM

BACKGROUND OF THE INVENTION

1. Field of the Invention

The invention relates to a novel composition and use thereof for insect control. More particularly, the invention relates to a composition of (E,Z)-8,10-pentadecadien-1-ol acetate and (E)-9-pentadecen-1-ol acetate, and use of the composition as an attractant, mating disruptant, and monitoring agent for the cranberry fruitworm.

2. Description of the Art

The cranberry fruitworm, *Acrobasis vaccinii* Riley, is a member of the Pyralidae family of the Lepidoptera (moths and butterflies). It occurs throughout the United States and Canada wherever its host plants occur. It is the most important pest of cranberries and blueberries and is capable of decimating these crops. Other host plants include huckleberries, dangle-berries, beach plums, and apples.

The cranberry fruitworm overwinters as a diapausing larva in a hibemaculum and is univoltine. A larva typically consumes 5–8 berries (Brodel and Roberts, *Cranberry Fruitworm*, Extension Bulletin, University of Massachusetts, East Wareham, Mass.). No attractant or pheromone has been known heretofore for the cranberry fruitworm, therefore, it was not possible to know, prior to crop damage, if cranberries, blueberries, or other host plants were infested with this insect, or whether or not control measures were required. What is needed is an effective attractant for detecting, monitoring and controlling this pest.

SUMMARY OF THE INVENTION

We have discovered that a composition of two compounds, (E,Z)-8,10-pentadecadien-1-ol acetate and (E)-9-pentadecen-1-ol acetate, in a particular ratio range, is a highly effective attractant for the male cranberry fruitworm. The composition of the invention is the first known chemical attractant for the cranberry fruitworm and provides, for the first time, a means for detecting, surveying, monitoring, and controlling this species.

The attractant composition of the invention provides a highly effective lure for use to detect and monitor the cranberry fruitworm to determine the presence of the pest and whether control measures are needed. Thus, the composition offers an important tool in an integrated pest management program for control of this pest. By monitoring pest populations with traps baited with the sex attractant composition, the numbers of insecticide applications can be reduced while increasing the effectiveness of control because insecticides are only applied when the cranberry fruitworm is present.

Further, when used in combination with a control agent for the cranberry fruitworm, such as a pesticide or biological control agent, the composition can be used as a direct control agent by attracting cranberry fruitworm males to a trap and incapacitating the insects so that they are not able to fertilize the females. Another use of the composition of the invention is for disruption of mating by confusion of cranberry fruitworm males.

In sum, the novel sex attractant composition provides a sensitive tool for the detection of the cranberry fruitworm and provides a means for population control and population density estimation of this pest. Its usefulness in eliciting a behavioral response when applied to a locus of cranberry fruitworm males suggests the following economic applications: (1) the detection of infestation outbreaks; (2) the monitoring of existing adult populations in order to predict future infestation levels for scheduling treatment the following year with larval insecticides or for treatment of moths in the current year with conventional pesticides or other control agents, (3) surveying to determine if this insect is established in a particular geographical location, and (4) the control of reproduction in adult populations either by direct disruption of mating through confusing or inhibitory properties, or by attracting a demographically significant portion of the male population for subsequent destruction or sterilization.

In accordance with this discovery, it is an object of the invention to identify for the first time a unique sex attractant composition for the cranberry fruitworm.

Another object of the invention is the provision of the composition as a detection, surveying, monitoring, or control agent for the cranberry fruitworm.

A further object of the invention is the provision of a cranberry fruitworm sex attractant for use with insecticides, biological control agents, or other toxicants, to attract and combat this pest.

Other objects and advantages of the invention will become readily apparent from the ensuing description.

DETAILED DESCRIPTION OF THE INVENTION

The attractant composition of the invention requires the presence of two compounds in the mixture: (E,Z)-8,10-pentadecadien-1-ol acetate (hereinafter I) and (E)-9-pentadecen-1-ol acetate (hereinafter II). The broad range of weight ratios of the compounds in the composition that is an effective attractant for cranberry fruitworm males is about 100:1 to 100:16 (I:II). This corresponds to a ratio range of about 100:2 to 100:32 (I:II) in the evaporating vapor when the composition is used in conjunction with a synthetic elastomer septum as the controlled release substrate. The preferred weight ratio range of the attractant composition is 100:2 to 100:8 (I:II), and more preferably 100:4 (I:II). This corresponds to a ratio range of about 100:4 to 100:16 (I:II) and 100:8 (I:II), respectively, in the evaporating vapor when the composition is used in conjunction with a synthetic elastomer septum as the controlled release substrate.

Figure 1:
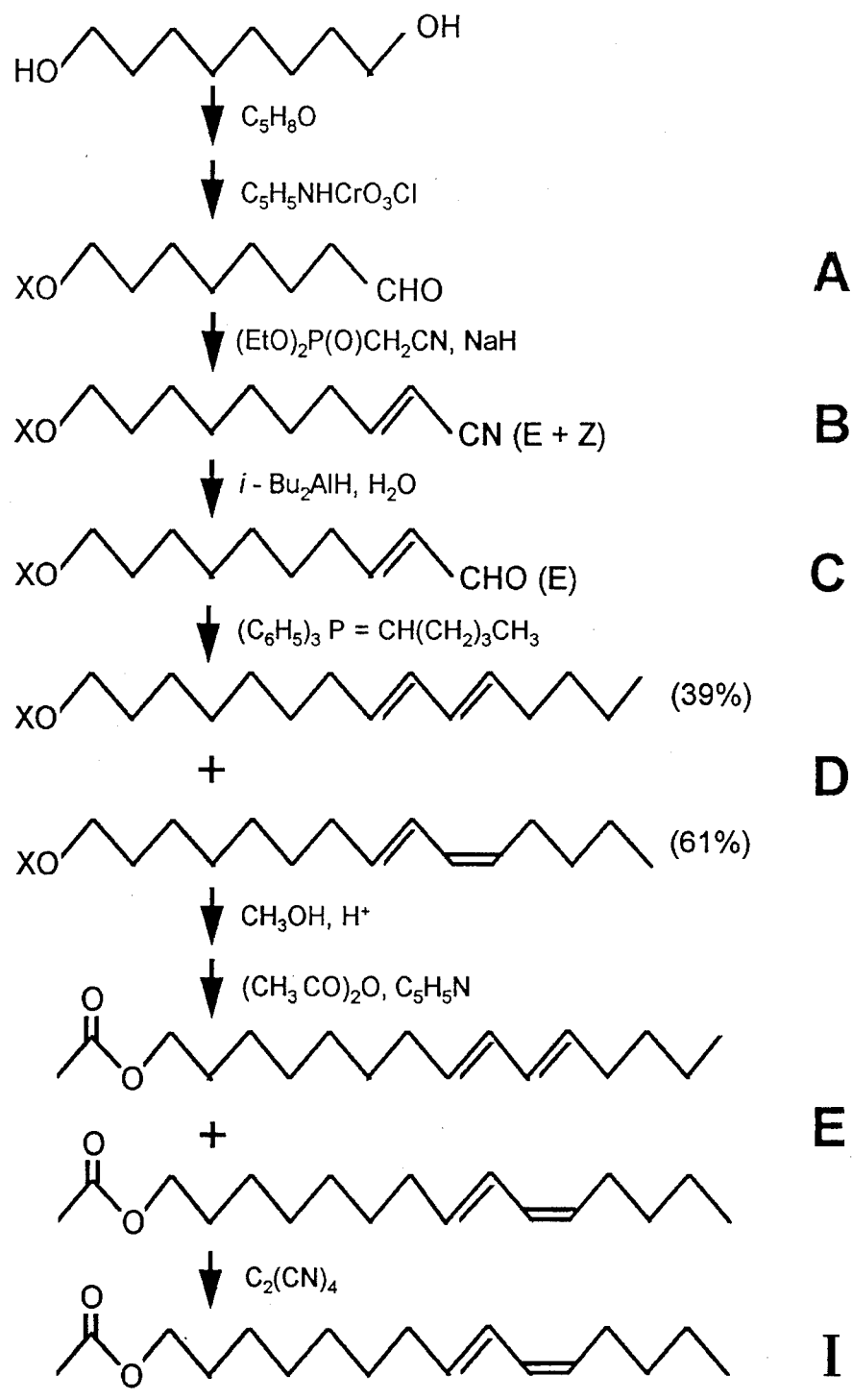
FIG. 1 illustrates the synthesis of (E,Z)-8,10-pentadecadien-1-ol acetate.

The synthesis of compound I, the major component of the attractant composition of the invention is illustrated in FIG. 1. In brief, 1,8-octanediol is reacted with dihydropyran in dichloromethane catalyzed by hydrochloric acid to give 8-[(tetrahydro-2H-pyran-2-yl)oxy]-1-octanol, which is reacted with pyridinium chlorochromate to give 8-[(tetrahydro-2H-pyran-2-yl)oxy]octanal (A). The octanal (A) is then reacted with diethylcyanomethylphosphate and sodium hydride to produce 10-[(tetrahydro-2H-pyran-2-yl)oxy]-2-decenitrile (B). Diisobutylaluminum hydride reduces nitrile (B) to an imine which upon hydrolysis yields the aldehyde (C). Wittig coupling of (C) with n-pentyl triphenylphosphorane gives the mixture of conjugated dienes (D)

which upon hydrolysis and acetylation give the two isomeric pentadecadien-1-ol acetates (E). The (E,E)-8,10-isomer is removed by Diels-Alder reaction with tetracyanoethylene to give pure (E,Z)-8,10-pentadecadien- 1-ol acetate (I). A detailed description of the synthesis of I is given in Example 4, below.

Compound II, the minor component of the attractant composition of the invention can be prepared synthetically in accordance with the procedure described by S. Voerman, *Agric. Ecosystems Environ.* 21:31–41 (1988), as follows: 1,8-Octanediol is converted to 8-chlorooctan-1-ol with concentrated hydrochloric acid in a continuous extractor containing petroleum ether (b.p 100°–140° C.) to extract the product. Dihydropyran is reacted neat with 8-chlorooctan-1-ol and a catalytic amount of hydrochloric acid to form the pyran derivative. The pyran derivative is added to a hexamethyl-phosphoric triamide solution of heptyne and butyl lithium. The pyran derivative, heptyne, and butyl lithium are in equimolar amounts. The product is the pyran derivative of 9-pentadecyn-1-ol which is reduced to the (E)-9-pentadecen-1-ol pyran derivative by sodium in a solution of liquid ammonia and tetrahydrofuran. The resultant product is converted to (E)-9-pentadecen-1-ol acetate by gentle heating in a solution of acetic acid and acetic anhydride (2:1).

In order to function as an attractant composition for the cranberry fruitworm, both I and II must be present in the mixture. As shown in the examples below, compound I, alone, failed to elicit upwind flight of males in flight tunnel tests (see Example 2), and traps baited with it did not catch males in field tests (see Example 3). When compound I was combined with II (100:4), male upwind flight response in flight tunnel tests was equivalent to responses obtained with extract of female sex pheromone glands. Traps baited with the combination caught large numbers of males in field tests (see Example 3, below).

Neither of the two compounds of the attractant composition of the invention have ever been reported to be attractants or pheromone components of any insect species, heretofore. Further, no one has reported isolation of a pheromone from Acrobasis species prior. The compound (Z)-9-pentadecen-1-ol acetate has been reported to attract a few members of a related species, *Acrobasis rufilimbalis* Wileman, into traps in field screening experiments (Mayer and McLaughlin, *Handbook of Insect Pheromones and Sex Attractants*, CRC Press Inc., Boca Raton, Fla. (1991), page 35). However, this compound is not attractive to cranberry fruitworm males and did not enhance the attractancy of the attractant composition of the invention (see flight tunnel tests, below). This is surprising in view of the fact that we found that this compound was tied as the second in abundance present in the extract of the female sex pheromone gland of the cranberry fruitworm (see Table 4 in Example 1, below).

The compounds in the two-component attractant composition described above are used in pure or substantially pure form. As used in the specification and the claims, the phrase "pure or substantially pure" means that compounds I and II are substantially free of undesirable masking or inhibitory effects with regard to the intended activity. Other compounds may be added to the composition provided they do not substantially interfere with the intended activity of the two-component composition of the invention. For example, as shown in Example 2, below, the inclusion of the other identified 15 carbon acetates with the two-component attractant composition of the invention did not increase or decrease response in the flight tunnel over that obtained without the inclusion of these compounds. Whether or not a compound interferes with attractant activity can be determined by routine tests in a flight tunnel or in the field as described in Examples 2 or 3, below.

USES OF THE ATTRACTANT COMPOSITION

The attractant composition of the invention may be used as a detecting agent, surveying agent, monitoring agent, or control agent for the cranberry fruitworm. In practice, the attractant composition is used as a trap bait or is otherwise applied to a locus of cranberry fruitworm males, that is, an area where the insects are present or when they may occur, e.g., a cranberry bog, blueberry field or other host plant field. The composition of the invention is used in an amount effective to induce the desired male response. In the case of an attractant response, an effective amount is defined as that quantity of the composition that attracts cranberry fruitworm males to the location of a bait at a rate significantly higher than males are attracted to a nonbaited location. Under typical field conditions, amounts of 100 to 3000 µg per septum using gray elastomeric septa (which corresponds to an evaporation rate of about 1 ng per hour to 30 ng per hour per septum at 20° C.) and preferably 300 to 1000 µg per septum (which corresponds to an evaporation rate of about 3 ng per hour to 10 ng per hour per septum) are effective. Factors such as population density, temperature, wind velocity, and rain will influence the response of the moths and thus the actual number of moths trapped. The amount of composition in a particular set of circumstances that will be within an effective range can be readily determined by a dose response field test as described in Example 3, below. Considering the long half-lives of 1,000–2,500 days at 20° C. expected from the two pheromone components in gray elastomer septa [McDonough, "Controlled Release of Insect Sex Pheromones from a Natural Rubber Substrate," pp. 106–124. In: P. Hedin (ed.). *Naturally Occurring Pest Bioregulators*, ACS Symposium Series No. 449, American Chemical Society, Washington, D.C. (1991); McDonough et al., *Journal of Chemical Ecology* 19:1737–1748 (1993)], doses of 300–1,000 µg per gray septum should provide an effective lure for an entire season.

In the case where the desired response is disruption of mating by confusing or inhibiting the male moth, an effective amount is defined as that quantity of the composition which permeates the atmosphere such that males are unable to orient to and inseminate females (i.e., disruption of mating) at a rate as high as males at a nontreated location. As with the attractant response, factors such as population density, temperature, wind velocity, and rain will influence the actual number of insects disrupted. The exact dose to use in any particular set of circumstances can be readily determined by a dose response field test.

It is envisioned that the attractant composition would be useful in detecting, surveying, monitoring, or controlling cranberry fruitworm populations when used in a pheromone controlled release substrate (CRS) which is used to control the evaporation rate of the composition. Preferred CRS are gray elastomer septa or other septa devoid of sulfur compounds. Typically, the composition is applied to septa in solution in a suitable carrier, that is, one that does not interfere with the activity of the composition, for example, an organic solvent such as dichloromethane or hexane. Examples of other CRS are polymer laminates, polyvinyl chloride pellets, and microcapillaries. The composition is applied to the CRS to provide a ratio of components in the evaporating vapor of about 1–30 ng per hour (I:II) and preferably about 3–10 ng per hour (I:II). Optimum attractant amounts can be readily determined by routine experimentation as illustrated in Example 3, below. CRS used for controlling populations by mating disruption include the aforenamed CRS or other CRS specifically designed for this purpose, e.g., sealed polyethylene tubes, containing an effective disruptant amount. A CRS may be used in conjunction with traps known in the art. Exemplary of such traps are the "Pherocon" 1C sticky trap.

When used as a detection, survey, or monitoring agent, traps are baited with the novel composition of the invention and the catch tabulated to determine size and location of infestation. Economic use of appropriate control agents can then be determined.

Use of the composition as a control agent can be carried out in several ways. One method is to use the composition to attract the insects to suitable substrates and subsequently or simultaneously expose the insects to insecticides which control the cranberry fruitworm. An effective amount of the insecticide is used, that is an amount that is lethal for an exposed insect or at least sublethal but sufficient to incapacitate the insect in regard to mating activity. Examples of useful insecticides are azinphosmethyl or other organophosphate insecticides (Tomlinson, *Journal of Economic Entomology* 53:1116–1119 (1960)). Insecticides can be used in traps baited with the composition, thereby minimizing the dissemination of the insecticide. It is also envisioned that chemosterilants could be used in conjunction with the composition to attract and sterilize male moths.

Another method to control the cranberry fruitworm using the composition of the invention is to detect the location and boundaries of localized cranberry fruitworm infestations, and then employ in the area biological control agents such as parasites or predators of the cranberry fruitworm.

The attractant composition may also be used to control the cranberry fruitworm by confusion of males, thus preventing mating. For example, one technique is to permeate the atmosphere e.g., by dispensing the composition throughout the crop canopy, with a sufficient amount of the composition to prevent males from locating the females or from orienting to and inseminating the females.

DISCOVERY OF THE ATTRACTANT COMPOSITION

Discovery of the attractant composition for the male cranberry fruit worm presented problems of particular difficulty. As discussed above, no attractant or pheromone had ever been previously reported for the cranberry fruitworm. Additionally, neither of the two compounds which comprise the attractant composition of the invention had ever before been reported to be attractants or pheromone components of any insect species and the only compound reported to be somewhat attractive to a related species was found not to be attractive to the cranberry fruitworm.

Further, attempts to discover an attractant for the cranberry fruitworm by investigating compounds present in the sex pheromone gland extracts of female cranberry fruitworms presented difficult problems. Isolation and identification of putative pheromone components from the cranberry fruitworm was particularly difficult because of the small numbers of insects available and the small amount of active components in the female sex pheromone gland, $5\times10^{-10}$ g (0.5 ng) of compound I and $2\times10^{-11}$ g (0.02 ng) of compound II. Identification of the major component (I) was accomplished with 60 female moths (30 in 1986 and 30 in 1987). Because of the small number of insects, chemical degradative studies of the pheromone to elucidate the structure were not possible. Electroantennographic analysis of fractions of sex pheromone gland extract collected from a gas chromatograph, followed by gas chromatographic-mass spectrometric (GC-MS) analysis indicated the major component was one of the 44 possible pentadecadien-1-ol acetates. This class of compounds had never been previously found to be attractants for any insect species. Identification of the major component was achieved by laboriously synthesizing 20 of the 44 possible structures. One of the 20 compounds matched the GC retention indexes and mass spectrum of the major sex pheromone component. However, this effort was not sufficient because the identified compound was not an attractant by itself either in flight tunnel bioassays or in field assays in blueberry fields or cranberry bogs. In 1989 and 1990 moths were again available and 100 females were obtained each year. GC-MS analysis showed the presence of other pheromonelike compounds in the extract of the sex pheromone glands. As discussed above, one of these, (Z)-9-pentadecen-1-ol acetate, had been shown to be attractive to a related insect species. However, we found that it was not an attractant for the cranberry fruitworm and did not confer attractancy on the main pheromone component. Another difficulty was the large number of pheromonelike compounds eventually identified in the extract of female sex pheromone glands, 17 in all (see Table 4 in Example 1, below). Only two of these compounds were found to be biologically active. The other 15 compounds only served to complicate identification of pheromone components.

Identification of the minor, but essential component of the attractant composition of the invention (II), was accomplished only after more insects became available in 1991. Even then the identification was difficult. It was accomplished first by bioassaying gas chromatographic fractions of female sex pheromone gland extracts in a flight tunnel. Unfortunately the insects did not respond in high or consistent numbers and many tests were necessary before the active fraction was identified. Then to identify the chemical components in the active fraction a mass spectral search in the Single Ion Monitor (SIM) mode was conducted on an extract of 500 female sex pheromone glands. From this analysis, three pentadecen-1-ol acetates and four pentadecadien-1-ol acetates were identified. Extensive flight tunnel bioassays testing various combinations showed that I and II were biologically active and all the other identified components were inactive.

EXAMPLES

The following examples are intended only to further illustrate the invention and are not intended to limit the scope of the invention which is defined by the claims.

Example 1

This example describes the isolation and identification of compounds present in the sex pheromone gland extract of female cranberry fruitworms.

Insect Collection and Handling. Each year in the springs of 1986 and 1987, 80–90 cranberry fruitworm hibernacula were collected from the soil of blueberry fields in Michigan and shipped to Yakima, Wash. in moist peat moss. In 1989 and later, cranberry fruitworm larvae were collected from infested cranberries from Massachusetts bogs and placed on hardware cloth over a tray of wet sand. Mature larvae upon leaving the berries fell through the cloth and formed hibernacula in the sand. The hibernacula were conditioned at 21° C. for 2 weeks, 15° C. for 2 weeks, 10° C. for 3 weeks, and 4° C. for 4 weeks. Then they were placed in moist peat moss and shipped to Yakima, Wash. where they were placed on a 5- to 6-cm layer of moist peat moss in covered clear plastic shoe boxes, and held in a rearing room at a temperature of 5° C., a relative humidity of 55–60%, and a 12:12 hour light-dark cycle. In 1989 and 1990, 300 hibernacula were obtained and in 1991, 3,000 hibernacula were obtained. As adults were needed, boxes were removed and placed in another facility at a temperature of 55° C. and a 13:11 hour light-dark cycle for a week and then at 21° C. and a 15:9 hour light-dark cycle. Emergent adults were collected daily at least 1 hour before the dark period and placed in individual vials. Usually, about 70% emergence of adults from hibernacula was obtained.

Collection of Sex Pheromone Gland Extracts. Female moths (2–3 days old) in their vials were collected 8 hours after the beginning of scotophase when they appeared to be "calling," and placed in a refrigerator to inactivate them. They were removed individually, and their terminal abdominal segments containing the sex pheromone gland were severed and steeped for 15–60 minutes in about 200 μl hexane. Then the hexane solution was removed with a syringe and kept in a freezer until analysis.

Gas Chromatography-Mass Spectrometry (GC-MS). A Hewlett-Packard (Avondale, Pa.) gas chromatograph (model 5790) with a quadrupole mass spectrometer (model 5970) was equipped with either a DB-1 or a DB-Wax capillary column, 60 m by 0.25 mm i.d. (J&W Scientific, Folsom, Calif.). For different analyses, both total ion abundance and single ion monitoring (SIM) were used.

Gas Chromatography-Electroantennography (GC-EAG). Fractions of extracts of sex pheromone glands were collected from a GC equipped with megabore capillary columns (15 m by 0.54 mm i.d.) (J&W Scientific, Folsom, Calif.). One series of collections were made with a DB-1 liquid phase and the other with a DB-Wax liquid phase. Fractions were collected in 3-mm-i.d., U-shaped, glass traps cooled by Dry Ice-acetone, and then dissolved in dichloromethane and deposited on the inside of glass tubes for EAG determinations.

Electroantennogram (EAG) Determinations. The EAG determinations of model compound profiles were made using the apparatus and procedure described by McDonough et al., *Journal of Chemical Ecology* 6:565–572 (1980) except that 60μg charges were used. Duplicate determinations were made for each compound. If the determinations were not close, a third determination was made. The saturated compounds were obtained from commercial sources, and the monoenes were synthesized by the procedure of Voerman, *Agric. Ecosystems Environ.* 21:31–41 (1988). The conjugated dienes were synthesized by the procedures of McDonough et at., *Journal of Chemical Ecology* 8:255–265 (1982), Ujvary et al., *Journal of Chemical Ecology* 11:113–124 (1985), and McDonough and Smithhisler, *Southwest. Entomol.* 14:153–157(1989), and the isomeric mixtures were produced as reported by McDonough et al., *Journal of Chemical Ecology* 19:1737–1748 (1993). All compounds were at least 98% pure by capillary gas chromatography and the monoenes contained 1% or less of their geometric isomers. The monoenes tested were the 12, 13, 14, 15, and 16 carbon acetates, and the 12, 14, 15, and 16 carbon alcohols. The dienes tested were the stereoisomeric mixtures of the positional isomers (6,8-, 7,9-, 8,10-, 9,11- and 10,12-) of pentadecadien-1-ol acetate. The (E,Z)-8,10-pentadecadien-1-ol acetate was of 92.6% isomeric purity.

Identification of the Major Sex Pheromone Component. In 1986, extracts of 20 female sex pheromone glands were collected in fractions from a gas chromatograph equipped alternately with a polar (DB-Wax) and a nonpolar (DB-1) column, and the EAG responses elicited by the fractions from each GC column were determined. Table 1 shows EAG responses relative to the fraction eliciting the greatest response (=100) of cranberry fruitworm males to gas chromatographic fractions of female sex pheromone gland extracts. On the DB-Wax column, the fraction with retention index ($I_x$) (Kovats, Chapter 7, *Advances in Chromatography*, Vol. 1, Marcel Dekker, New York (1965))values of 2347–2419 elicited the greatest response, and on the DB-1 column, the fraction with $I_x$ values of 1834–1930 elicited the greatest response. The two most active fractions from the EAG analysis were recovered, combined, and analyzed by GC-MS (DB-1 column). Based on the mass spectra, most of the compounds found within the active $I_x$ range were GC column bleed, phthalates, or hydrocarbons, but in addition, a pentadecadien-1-ol acetate was identified ($M^+$, 266; $M^+$-60, 206; $CH_3CO_2H_2^+$, 61) with a retention index of 1912. The difference between the retention index values of the fractions eliciting the greatest EAG responses on the polar and nonpolar columns, and the easy detectability of the $M^+$ ion of the pentadecadien-1-ol acetate indicated that the double bonds were conjugated.

Figure 2:
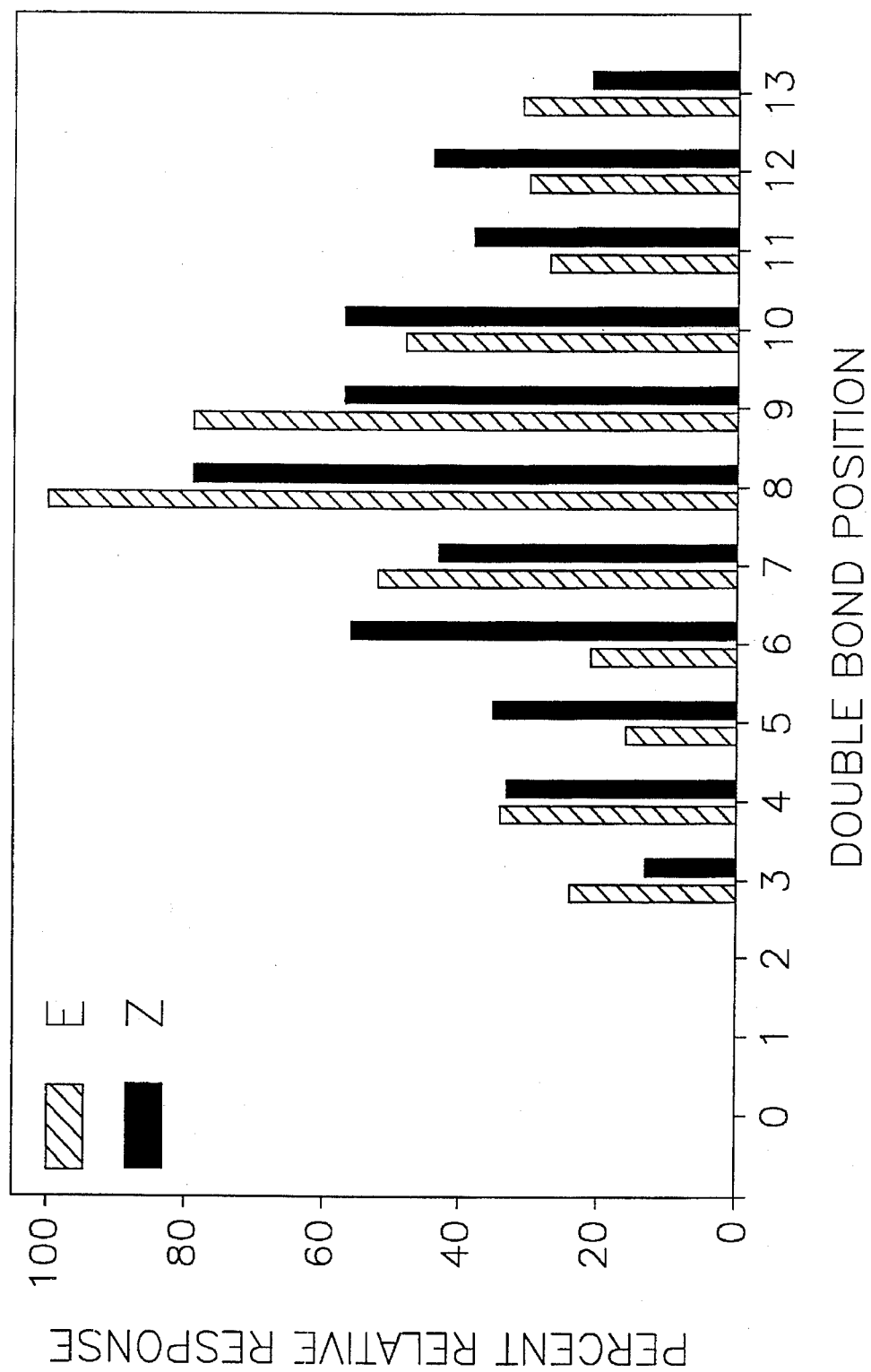
FIG. 2 shows the electroantennogram responses of male cranberry fruitworms to pentadecen-1-ol acetates. Numbers indicate double bond position. Z-isomers are listed after E-isomers.

In an attempt to determine the double bond positions in the diene, the EAG responses to pentadecen-1-ol acetates were determined as described above. The results are shown in FIG. 2. The strong response to the E8-isomer suggested this as one of the double bond positions, but there was no distinction between the 6- or the 10-isomers as indicators of the other double-bond position.

Because of limited availability of insects and the small amount of the pentadecadien-1-ol acetate per insect (ca. 0.5 ng), the double-bond positions of the pentadecadien-1-ol acetate could not be determined by ozonolysis. Therefore, all of the stereoisomers of the pentadecadien-1-ol acetates with double bonds in the 6,8-, 7,9-, 8,10-, 9,11-, and 10,12-positions were synthesized, and compared to the natural compound. The retention indexes of these isomers on the polar (DB-Wax) and nonpolar (DB-1) GC columns are given in Table 2. GC-MS analysis of sex pheromone gland extract from the 1987 batch of insects showed the presence of two pentadecadien-1-ol acetates in a ratio of 100:6. The major compound had a retention index of 1912.2 on DB-1 and 2385.7 on DB-Wax and the minor compound had a retention index of 1936.8 on DB-1 and 2422.5 on DB-Wax. The best fit of these indexes with those of Table 2 corresponded to the E8,Z10- and E8,E10-isomers for the major and minor compounds, respectively.

When EAG responses elicited by the stereoisomeric mixtures of the positional isomers of the pentadecadien-1-ol acetates (6,8-, 7,9-, 8,10-, 9,11-, and 10,12-) were compared, the 8,10-pentadecadien-1-ol acetates elicited 20–40% stronger than the other stereoisomeric mixtures. The response to the isomeric mixture of 8,10-pentadecadien-1-ol acetates was ca. 80% of that of (E)-8-pentadecen-1-ol acetate. Purified (E,Z)-8,10-pentadecadien- 1-ol acetate (compound I) (92.6% EZ) elicited about a 10% greater response than (E)-8-pentadecen-1-ol acetate.

Traps baited with (E,Z)-8,10- and (E,E)-8,10-pentadecadien-1-ol acetates in a 100:6 ratio at a 1 mg dose per gray septum were tested in infested blueberry fields during the 1987 flight season, but no fruitworms were caught in 10 traps, therefore indicating that there was probably one or more essential components missing.

Identification of the Minor Sex Pheromone Component. In EAG studies, none of the other series of compounds (12, 13, 14, and 16 carbon acetates and 12, 14, 15, and 16 carbon alcohols) elicited intense responses compared to 15-carbon acetates. Other compounds, eliciting moderately intense EAG responses with responses compared to (E)-8-pentadecen-1-ol acetate (100%), were: (Z)-6-tridecen-1-ol acetate (74%), (E)-8-tetradecen-1-ol acetate (62%), and (E)-8-tridecen-1-ol acetate (59%).

Flight Tunnel Tests. To gain information about other possible pheromone components, fractions of sex pheromone gland extract were collected from the gas chromatograph (DB-1 column), and assayed in a flight tunnel. The tunnel was constructed as described by Miller and Roelofs (*Journal of Chemical Ecology* 4:187–198 (1978)) and maintained at 21° C. Males were released in groups of three. The test compounds were formulated either on dental rolls or in gray elastomeric septa (formulation number 1888, size 6 mm by 10 mm, West Co. Phoenixville, Pa.) (Brown and McDonough, *Journal of Economic Entomology* 79:922–927 (1986)). These tests are summarized in Table 3. (Six cranberry fruitworm males were used in each test.) The results were not entirely consistent because fraction 3 (which contained the pentadecadien-1-ol acetates), and fractions 1+3 did not elicit response, but responses were only obtained from other test mixtures in which fraction 3 was present. Because the pentadecadien-1-ol acetates alone did not elicit response, these results indicated that one of the other components necessary for pheromonal activity was probably in fraction 3.

In preparation for a mass spectral analysis search for minor components, sex pheromone gland extract was chromatographed using liquid chromatography on a small silica gel column. The column, tapered at one end, was 8 mm in diameter and about 20 cm long. The tapered end was plugged with glass wool and filled with about 0.5 cm of sodium sulfate, 0.6 gm of silica gel (ca. 7.5 cm), and topped with about 1.0 cm of sodium sulfate. The volume of the column was 1.2 ml. The column was washed with 4.8 ml of dichloromethane-hexane (4:10), followed by 3.6 ml of hexane. The sex pheromone gland extract (100 female equivalents) in 200 µl of hexane was added to the column, which was eluted with three 1.2 ml portions of hexane, four 1.2 ml portions of dichloromethane-hexane (3:10), and finally with five 1.2 ml portions of dichloromethane. The alcohol and ester fractions were combined. The esters eluted in the dichloromethane-hexane fractions, and the alcohols eluted in the dichloromethane fractions. The recovery of nanogram quantities of model compounds by this procedure was 45%. As an aid to the determination of retention indexes, hydrocarbon standards were added to the combined fractions, which were concentrated and then analyzed by GC-MS. The previously found compounds, I and (E,E)-8,10-pentadecadien-1-ol acetate, were again detected. In addition pentadecan-1-ol acetate (M–60=210; M–60–28=182; $CH_3CO_2H_2$=61; $I_x$=1890.4 versus $I_x$=1890.3 for the standard) and (Z)-9-pentadecen-1-ol acetate (M–60=208; M–60–28=180; $CH_3CO_2H_2$=61; $I_x$=1871.4 versus 1871.5 for the standard) were detected in ratios of 15% and 23%, respectively, relative to I.

The four identified components of the sex pheromone gland were formulated in the ratios found in the extract at a dose of 1 mg/septum of I to test their ability to evoke trap catch of males. Ten traps baited with the lures were tested in cranberry bogs known to be infested with cranberry fruitworms, but again no males were caught.

When more hibernacula were available, the first part of the experiment of Table 3 was repeated, and fraction 3 (15 female equivalents) elicited 33% upwind flight and 30% contacting the source (n=27). The combined fractions 1–5 gave 57% upwind flight and 57% contacting the source (n=35). Fractions 1, 2, 4, and 5 elicited no responses. These results reinforced the previous conclusion that the components necessary for upwind flight to the pheromone source were in fraction 3.

To search further for minor pheromone component(s), an extract of 489 female sex pheromone glands was collected in two fractions from a gas chromatograph equipped with a DB-Wax column. The first fraction covered retention index values of 2158–2337 and included the pentadecen-1-ol acetates. The second fraction covered the retention index values of 2340–2355 and included the pentadecadien-1-ol acetates. Each of these fractions was individually analyzed by GC-MS (DB-1 column) in the single ion monitor mode. For the diene fraction, the ions monitored were 266, 206 and 61. Besides I and (E,E)-8,10-pentadecadien-1-ol acetate, (Z,E)-8,10-pentadecadien-1-ol acetate, and (Z,Z)-8,10-pentadecadien-1-ol acetate were detected. The ratios were: 100:1:2:12 (EZ:ZE:ZZ:EE). For the monoene fraction, the ions monitored were 208, 180, and 61. Besides (Z)-9-pentadecen-1-ol acetate, (Z)-8-pentadecen-1-ol acetate and II were detected. The ratios were 100:14:18 (Z9:Z8:E9).

Other Compounds in the Female Sex Pheromone Gland Extract. During the course of these studies, other pheromonelike compounds were detected in the extract of the female sex pheromone gland. To further identify such compounds, 5 fractions, covering retention index values of 1350–1550, 1550–1750, 1750–1950, 1950–2150, and 2150–2350, were collected from a GC equipped with a DB-1 column. Each fraction was individually analyzed by GC-MS (DB-1 column; total ion monitor mode). The compounds found in these and previous analyses are summarized in Table 4. The monoene and saturated acetates were identified by the M–60, M–60–28, and 61 m/z values and by retention index, and the alcohols were identified by the M–18 and M–18–28 m/z values and by retention index.

TABLE 1

| Fraction no. | DB-Wax | | DB-1 | |
|---|---|---|---|---|
| | $I_x$ Range | Relative EAG Response | $I_x$ Range | Relative EAG Response |
| 1 | 0–1910 | 0.9 | 0–1613 | 3.4 |
| 2 | 1910–2064 | 4.6 | 1613–1730 | 9.4 |
| 3 | 2064–2176 | 12.5 | 1730–1834 | 12.0 |
| 4 | 2176–2268 | 16.1 | 1834–1930 | 100 |
| 5 | 2268–2347 | 23.4 | 1930–2029 | 31.4 |
| 6 | 2347–2419 | 100 | 2029–2200 | 31.3 |
| 7 | 2419–2560 | 43.2 | | |

TABLE 2

| GC Column and Double Bond Configuration | $I_x$ Values at Given Bond Positions of Pentadecadien-1-ol Acetates | | | | |
|---|---|---|---|---|---|
| DB-1 | 6,8- | 7,9- | 8,10- | 9,11- | 10,12- |
| ZE | 1899.2 | 1902.4 | 1905.4 | 1909.7 | 1916.2 |
| EZ | 1902.3 | 1906.4 | 1911.7 | 1918.1 | 1924.6 |
| ZZ | 1922.4 | 1923.9 | 1926.7 | 1929.7 | 1931.7 |
| EE | 1937.8 | 1937.8 | 1936.6 | 1935.0 | 1935.3 |
| DB-Wax | | | | | |
| ZE | 2368.9 | 2373.3 | 2377.8 | 2381.0 | 2395.9 |

TABLE 2-continued

| GC Column and Double Bond Configuration | $I_x$ Values at Given Bond Positions of Pentadecadien-1-ol Acetates | | | | |
|---|---|---|---|---|---|
| EZ | 2375.2 | 2381.7 | 2388.1 | 2395.4 | 2406.2 |
| ZZ | 2400.4 | 2402.4 | 2405.9 | 2409.1 | 2415.1 |
| EE | 2425.5 | 2426.6 | 2425.8 | 2419.7 | 2426.7 |

TABLE 3

| GC Fraction No. | $I_x$ Range (DB-1) | % Response in Flight Tunnel |
|---|---|---|
| 1 | 1650–1750 | 0 |
| 2 | 1750–1850 | 0 |
| 3 | 1850–1950 | 0 |
| 4 | 1950–2050 | 0 |
| 5 | 2050–2150 | 0 |
| 1 + 2 + 3 + 4 + 5 | | 50 |
| 1 + 3 | | 0 |
| 2 + 3 | | 33 |
| 4 + 3 | | 33 |
| 5 + 3 | | 33 |
| 2 + 4 | | 0 |

TABLE 4

| Compound | Relative Amount |
|---|---|
| (E,Z)-8,10-pentadecadien-1-ol acetate | 100 |
| (Z,E)-8,10-pentadecadien-1-ol acetate | 1 |
| (E,E)-8,10-pentadecadien-1-ol acetate | 12 |
| (Z,Z)-8,10-pentadecadien-1-ol acetate | 2 |
| (Z)-9-pentadecen-1-ol acetate | 23 |
| (Z)-8-pentadecen-1-ol acetate | 3 |
| (E)-9-pentadecen-1-ol acetate | 4 |
| a heptadecen-1-ol acetate | 4 |
| a heptadecen-1-ol acetate | 4 |
| a dodecen-1-ol acetate | 8 |
| tetradecan-1-ol acetate | 3 |
| pentadecan-1-ol acetate | 15 |
| hexadecan-1-ol acetate | 10 |
| heptadecan-1-ol acetate | 8 |
| dodecan-1-ol | 6 |
| tetradecan-1-ol | 5 |
| hexadecan-1-ol | 23 |

Example 2

This example describes the study of the response of adult male cranberry fruitworms in a flight tunnel to pheromone components.

Flight tunnel tests were conducted with the newly discovered components. The isomeric purity of I in these tests was 92.6% (1.8% ZE, 1.8% EE, 3.8% ZZ). When I was tested in combination with (E,E)-8,10-pentadecadien-1-ol acetate, pentadecan-1-ol acetate, (Z)-9-pentadecen-1-ol acetate, (Z)-8-pentadecen-1-ol acetate, and II in a ratio of 100:12:15:23:3:4, respectively, at a dose of 12 ng I on a dental roll, 76% of males flew upwind and 38% contacted the source (n=21). When all of the components except II and I were removed, leaving I:II (100:4), male upwind flight response in flight tunnel tests was equivalent to those obtained with extract of female sex pheromone glands (synthetic, 62%; natural, 51% ).

Example 3

The following example describes field tests of the attractant composition of the invention.

Field Tests. Candidate lures in 100 μl dichloromethane were impregnated into gray elastomeric septa; dichloromethane alone was added to control septa. Pherocon 1C sticky traps (Trece Corp., Salinas, Calif.) were used. Traps were suspended from a moveable metal arm (an 18 by 23 cm shelf bracket) attached by a metal hose clamp to a 120-cm-long wooden broom handle driven into the ground. This arrangement allowed the traps to be positioned at the top of the plant canopy, where most flight activity was believed to occur. There were 24 traps per test deployed at approximately 10-m intervals in either an 8 by 3 or a 6 by 4 arrangement, or 30 traps per test deployed in a 6 by 5 arrangement. The position of each trap in the experimental plot was drawn randomly. There were four replicates of each test composition, and the trap data were transformed by $(x+0.5)^{0.5}$ and compared by Duncan's *Biometrics* 11:1–41 (1955) multiple-range test (p=0.05). Lures were tested in blueberry fields in Michigan and in cranberry bogs in Massachusetts.

Results. In 1992 traps baited with I and II in gray septa were tested in cranberry bogs to determine the most effective ratio of the pheromone components Table 5). The two 1992 tests were conducted in the same bog early and late in the season (top and bottom). In the first test, the most effective ratios were 100:2 to 100:8, although the 100:12 ratio only separated out statistically from the 100:2. In the second test, the 100:2 and 100:4 ratios elicited greater trap catch than the other ratios. Taken together these tests indicate that the titer of I relative to II (100:4), estimated from the mass spectral data, is a reasonable ratio for the most effective lure. In 1993, tests were conducted to determine the most effective dosage (Table 5). The two 1993 tests were conducted in 2 different bogs from June 20 to July 28. Between 100 and 3,000 μg/septum, there was no difference in trap catch in either test.

TABLE 5

| Composition | Total Trap Catch |
|---|---|
| 1992 Tests | |
| 300 μg I + 6 μg II (100:2%) | 156a[1] |
| 300 μg I + 12 μg II (100:4) | 97ab |
| 300 μg I + 18 μg II (100:6) | 68ab |
| 300 μg I + 24 μg II (100:8) | 89ab |
| 300 μg I + 36 μg II (100:12) | 34bc |
| 0 μg I + 0 μg II | 2c |
| 1000 μg I + 0 μg II (100:0) | 0a |
| 1000 μg I + 20 μg II (100:2) | 10ab |
| 1000 μg I + 40 μg II (100:4) | 25b |
| 1000 μg I + 80 μg II (100:8) | 3a |
| 1000 μg I + 160 μg II (100:16) | 1a |
| 0 μg I + 0 μg II | 1a |
| 1993 Tests | |
| 0 μg I + 0 μg III | 0a |
| 100 μg I + 4 μg II | 239b |
| 300 μg I + 12 μg II | 383b |
| 1000 μg I + 40 μg II | 357b |
| 3000 μg I + 120 μg II | 360b |
| 0 μg I + 0 μg II | 0a |
| 100 μg I + 4 μg II | 86b |
| 300 μG I + 12 μg II | 131b |
| 1000 μg I + 40 μg II | 137b |
| 3000 μg I + 120 μg II | 163b |

[1]Catches followed by the same letter were not significantly different (P = 0.05).

Example 4

The following example describes the synthesis of (E,Z)-8,10-pentadecadien-1-ol acetate.

8-[(Tetrahydro-2H-pyran-2-yl)oxy]-1-octanol. 1,8-Octanediol (16.8 g) (115 mmol) and 4.83 g of dihydropyran (57.5 mmol) in 1400 ml of dichloromethane containing 5 drops of concentrated HCl were stirred for 2 hours. Then 10 g of $NaHCO_3$ were stirred in and the solution was filtered. Dichloromethane was removed with a rotary evaporator, and the resulting residue was triturated with pentane; the undissolved solid was 1,8-octanediol. The solid was filtered from the pentane solution, and the pentane was removed with a rotary evaporator to give 13.2 g (99.8%) of crude product oil.

8-[(Tetrahydro-2H-pyran-2-yl)oxy]octanal (A). 8-[(Tetrahydro-2H-pyran-2-yl)-1-octanol (13.2 g) (57.4 mmol) in 75 ml of dichloromethane, that had been dried by distillation from $P_2O_5$, was added to a stirred solution of 18.6 g of pyridinium chlorochromate and 1.41 g of sodium acetate in dried dichloromethane (E. J. Corey and J. W. Suggs, *Tetrahedron Letters* 31:2647–2650 (1975)). After 2 hours, 400 ml of anhydrous ether were added; the solution was filtered, and the solvent was removed with a rotary evaporator. The residue was extracted with hexane, and the hexane was removed to give the crude product which was then purified by liquid chromatography. The yield was 8.0 g (61%). IR: 2700 $cm^{-1}$(w) and 1725 $cm^{-1}$(s), aldehyde; no 3330 $cm^{3-1}$ absorption for alcohols; typical tetrahydropyranyl ether pattern from 1470 to 1250 $cm^{-1}$.

10-[Tetrahydro-2H-pyran-2-yl) oxy]-2-decenenitrile (B). A mixture of 2 g (66 mmol) of NaH (80% dispersion in oil) in 90 ml anhydrous ether and 30 ml dry tetrahydrofuran was chilled and stirred under nitrogen in an ice bath. Diethyl cyanomethylphosphonate (11.7 g, 66 mmol) in 10 ml dry ether was added dropwise; a thick salt formed. After the addition was complete, the mixture was stirred for 1 hour at room temperature, and then cooled to below 15° C. The octanal (A) (6.9 g, 30 mmol) in 10 ml anhydrous tetrahydrofuran was added dropwise during about 30 minutes, and the mixture was stirred vigorously at room temperature for 2 hours. After the reaction mixture was quenched with methanol (1.5 ml), the solution was concentrated with a rotary evaporator and extracted with water (100 ml). The water and organic phases were separated, and the water phase was extracted three times with ether. The combined ether and organic phases were extracted once with water, then with saturated sodium chloride solution, and then dried with sodium sulfate. The solution was filtered, and the solvent was removed by a rotary evaporator, giving 9.0 g crude product (4.6 g of B by GC analysis) which was purified by liquid chromatography (elution from silica gel with 15% ether/hexane). IR: 2180 $cm^{-1}$, nitrile; 1620 $cm^{-1}$, double bond; typical tetrahydropyranyl ether pattern from 1470 to 1250 $cm^{-1}$. GC-MS: base peak m/z=85 (pyran fragment); m/z=101 and 150 typical of pyran fragmentation; 250 (M−1) and 251 ($M^+$). The yield of purified product was 4.2 g (57%).

10-[Tetrahydro-2H-pyran-2-yl)oxy]-2-decenal (C). Five ml (28.5 mmol) of diisobutylaluminum hydride in 20 ml anhydrous hexane were added dropwise during 30 minutes to a stirred solution of 4.2 g (17.2 mmol) of the decenenitrile (B) at −10° C. in 75 ml anhydrous hexane under argon. After the solution was stirred for 3 hours at −10° C. and 1 hour at 0° C., it was cooled to −10° C. and 1 ml isopropanol was added dropwise, and then 6 ml water were added dropwise. The resultant mixture was poured over a stirred mixture of 25 g ice and 7.6 ml acetic acid. After the mixture was stirred vigorously for 10 minutes, the aqueous and organic phases were separated; and the aqueous phase was extracted with hexane. The hexane extracts and the organic phase were combined and washed successively with 1N hydrochloric acid, water, saturated sodium bicarbonate, and saturated sodium chloride solution. The solution was dried over sodium sulfate. Solvent was removed with a rotary evaporator giving 4.5 g of crude decenal (C). IR: 2700 $cm^{-1}$(w) and 1690 $cm^{-1}$(s), aldehyde; 1630 $cm^{-1}$, double bond; typical tetrahydropyranyl ether pattern from 1470 to 1250 $cm^{-1}$. GC-MS: one GC peak showing typical MS pyran fragmentation, 85 (base peak), 101; and 253 (M−1). GC analysis showed one peak corresponding to 3of product (72% yield).

1-[Tetrahydro-2H-pyran-2-yl)oxy]-8,10-pentadecadiene (D). Pentyltriphenylphosphonium bromide (17.6 gm, 42.5 mmol) in 270 ml dry tetrahydrofuran was stirred in a three-neck flask under nitrogen at room temperature for 30 minutes. The bromide did not completely dissolve. n-Butyllithium (27.4 ml of 1.6M in hexane, 43.8 mmol) was added by syringe through a rubber septum on one neck of the flask. The solution became deep red, and the remainder of the bromide dissolved. The decenal (C) (4.5 g crude, 3.1 g actual) in 40 ml tetrahydrofuran was added dropwise and the mixture was stirred for 1 hour after the addition was complete. Excess phosphorane was discharged with acetone, and the solvent was removed on a rotary evaporator. The residue was extracted with water and pentane. Combined pentane fractions were dried over sodium sulfate. The pentane was removed on a rotary evaporator leaving 5.9 g crude product oil (D).

8,10-Pentadecadien-1-ol acetate (E). The pentadecadiene (D) (5.9 g) in 200 ml methanol containing eight drops concentrated HCl was refluxed for 15 minutes. After the solution was cooled, 400 ml of water were added, and the mixture was extracted three times with hexane. The hexane extract was dried over sodium sulfate, and the hexane was removed with a rotary evaporator leaving 3.1 g of crude 8,10-pentadecadienol, which was purified by silica gel liquid chromatography. Unwanted side products were eluted with 10% ether/hexane, and the alcohol was eluted with 50% ether/hexane, giving 2.5 g (66% yield based on the decenenitrile (B)). 8,10-Pentadecadienol in 75 ml pyridine and 5 ml acetic anhydride was refluxed 1.5 hours. After the solution was cooled, 200 ml hexane was added, and the mixture was extracted successively with water, 6N hydrochloric acid (twice), and water. The pentane phase was dried over sodium sulfate, filtered, and the pentane was removed by rotary evaporation, leaving crude product, which was purified by silica gel liquid chromatography (elution in 10% ether/hexane); the yield was 2.8 g (94% based on the alcohol). The product was 39% EE and 61% EZ by GC analysis.

(E,Z)-8,10-Pentadecadien-1-ol acetate (I). The acetate (E), 2.2 g (8.27 mmol) was stirred with 0.43 g (3.3 mmol) of tetracyanoethylene in 20 ml of dichloromethane for 3 hours. The Diels-Alder adduct was separated from the EZ isomer by liquid chromatography on silica gel. The yield was 1.1 g of I. The isomeric purity was 96.4% EZ, 0.6% ZE, 2.4% ZZ, and 0.7% EE.

What is claimed is:

1. An attractant composition for male cranberry fruitworm moths, which comprises a mixture of pure or substantially pure (E,Z)-8,10-pentadecadien-1-ol acetate (I) and pure or substantially pure (E)-9-pentadecen-1-ol acetate (II) in a weight ratio range of about 100:1 to 100:16 (I:II).

2. The composition of claim 1 wherein the weight ratio range is about 100:2 to 100:8 (I:II).

3. The composition of claim 1 wherein the weight ratio is about 100:4 (I:II).

4. The composition of claim 1 which further includes an organic solvent as a carrier for said composition.

5. The composition of claim 1 in combination with an effective insecticidal amount of an insecticide for the cranberry fruitworm.

6. A method of attracting male cranberry fruitworms, which comprises placing in a locus of male cranberry fruitworm moths a controlled release substrate (CRS) having an effective attractant amount of a composition comprising pure or substantially pure (E,Z)-8,10-pentadecadien-1-ol acetate (I) and pure or substantially pure (E)-9-pentadecen-1-ol acetate (II) mixed in a weight ratio to provide a vapor ratio of I:II of about 100:2 to 100:32.

7. The method of claim 6 wherein said vapor has a ratio of I:II of about 100:4 to 100:16.

8. The method of claim 6 wherein said vapor has a ratio of I:II of about 100:8.

9. A method of attracting male cranberry fruitworms, which comprises applying to a locus of male cranberry fruitworm moths elastomeric septa having an effective attractant amount of the composition of claim 1.

10. A method of disruption of mating of cranberry fruitworms, which comprises applying to a locus of adult male cranberry fruitworms an effective disruptant amount of the composition of claim 1.

11. A method for trapping male cranberry fruitworms, which comprises baiting a trap with an effective attractant a mount of the composition of claim 1.

* * * * *